Figure 1:
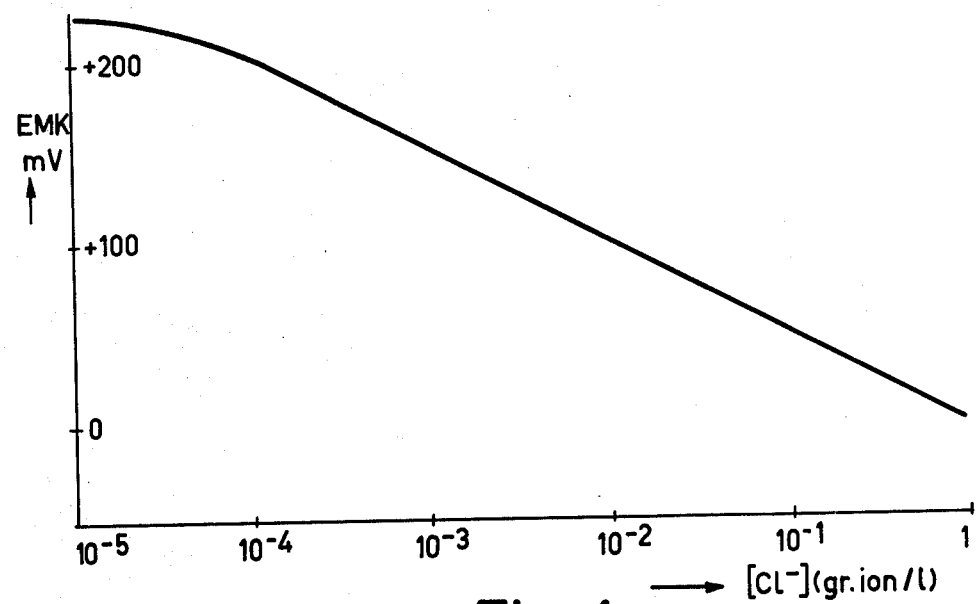

United States Patent [19]
Van de Leest et al.

[11] 4,096,049
[45] Jun. 20, 1978

[54] METHOD FOR PRODUCING AN ION-SELECTIVE ELECTRODE

[75] Inventors: Renaat Edmond Van de Leest; Leopold Heijne, both of Eindhoven, Netherlands

[73] Assignee: U.S. Philips Corporation, New York, N.Y.

[21] Appl. No.: 689,944

[22] Filed: May 25, 1976

[30] Foreign Application Priority Data

May 30, 1975 Netherlands .................. 7506410

[51] Int. Cl.$^2$ .................. G01N 27/46; B05D 3/04
[52] U.S. Cl. .................. 204/195 M; 204/1 T; 204/56 R; 427/248 E; 427/248 J; 427/255; 427/294; 427/399
[58] Field of Search .................. 204/195 M, 56 R, 94; 427/248 E, 248 J, 255, 294, 399

[56] References Cited

U.S. PATENT DOCUMENTS

| | | | |
|---|---|---|---|
| 3,563,874 | 2/1971 | Ross et al. | 204/195 M |
| 3,591,464 | 7/1971 | Frant et al. | 204/195 M |
| 3,716,403 | 2/1973 | Braun | 204/195 M |
| 3,822,198 | 7/1974 | Bauke | 204/195 M |
| 3,892,833 | 7/1975 | Hattori et al. | 204/195 M |

*Primary Examiner*—T. Tung
*Attorney, Agent, or Firm*—Frank R. Trifari; Norman N. Spain

[57] ABSTRACT

The production of an ion-selective electrode for selective measuring the concentration of an ion in a solution of a mixture of ions, consisting of silver sulphide as matrix material, which is superficially converted into a hardly soluble substance which has one ion in common with the matrix material.

2 Claims, 2 Drawing Figures

METHOD FOR PRODUCING AN ION-SELECTIVE ELECTRODE

The invention relates to a method for producing an ion-selective electrode and the electrode obtained by this method.

From United Kingdom Patent Specification No. 1,324,839 such electrodes are known for the selective measurement of concentrations of a given ion in a mixture of different ions, which electrode consists of at least two layers impermeable to liquid, which layers consist of monocrystalline, polycrystalline, vitreous-crystalline or vitreous materials, which materials have a common ion.

The object of this construction is to improve the strength of the electrode because many electrode materials in the form of thin layers lack the required strength to enable their use as self-supporting electrodes. Therefore a material which has the required strength is used as support.

The known electrodes are manufactured by introducing the weighted quantity of material in powder form into the pressing mould and to apply on top of that a uniform thick layer of the second material, after the first layer has been roughened in order to obtain a proper contact. The whole is thereafter compressed at a higher pressure, and, optionally, at an elevated temperature.

Also electrodes have been described which consist of a mixture of two of such substances. (J. W. Ross in R. A. Durst : Ion-selective electrodes, Chapter 2, NBS Special Public. 314 (1969)).

The applicant has ascertained that pressing resulted in products with different properties. These techniques yield electrodes having a rather moderate sensitivity and a slow response. If AgCl is used as material for the support, the internal resistance is rather high, which promotes a slow response.

The invention now provides a method for producing an ion-selective electrode having a large specificity, a large and reproducable sensitivity and a rapid response.

According to the invention such an electrode, consisting of silver sulphide as matrix material provided with at least one layer having a total thickness between 0.1 and 100 $\mu$m of a substance which has one ion in common with the adjacent material, whilst the layer which is in contact with the measuring medium has a solubility product which is smaller than $10^{-9}$ at room temperature, is produced owing to the fact that the layer or layers is/are obtained by converting the matrix material or any intermediate layers already applied thereon superficially or an intermediate layer applied on the matrix material wholly, chemically or electrochemically into the substance with an ion common with the adjacent material, said substance being rather insoluble in the measuring environment.

The silver sulphide has a specific ion conductivity at room temperature of approximately $10^{-5}$ mho.cm$^{-1}$ besides electron conduction. Ion conduction is essential for such a ion-selective electrode.

The active substance which forms the outer layer of the electrode need not have a high ion conduction. The optimum thickness of the layer depends on the specific ion conductivity: the lower it is the thinner the layer is preferably chosen.

In Applicant's UK Patent application No. 76/2321—U.S. patent application Ser. No. 640,704, filed Dec. 15, 1975, an electrode is described having a matrix material with a specific ion conductivity of at least $2 \times 10^{-4}$ mho-cm$^{-1}$. This higher conductivity results in a still faster response and a still higher sensitivity of the electrode than for that according to the present invention. The latter, however, is already considerably better in this respect than the electrodes known sofar.

Below some examples are given to illustrate the invention.

EXAMPLE 1

Each time 1 g Ag$_2$S in powder form was pressed with a diameter of 8 mm with a silver contact at a force of 15000 Newton. Thereafter, the whole was kept into contact with gaseous Cl$_2$, Br$_2$ or I$_2$ respectively for one hour at a temperature of 150°, 100° and 100° C respectively. The average thickness of the layers obtained was 5 $\mu$m.

According to an alternative method a tablet pressed in the above manner with a constant EMF (indicated in the drawing by EMK) was kept against a platinum counter-electrode in a solution of bromide or iodine ions, which caused Ag$^+$ ions to be produced, which thereafter reacted with the said ions under the formation of an active layer. Another possibility is the formation of the layer by means of a current flow at a constant current.

Four different electrodes, consisting of an Ag$_2$S matrix having an AgCl coating, produced to the method described, were used as electrodes for measuring Cl$^-$-concentrations in the range of $10^{-5}$ to 1 gramion/l in solutions which also contained $10^{-1}$ moles/l NaNO$_3$. FIG. 1 shows the sensitivity of the measurements obtained : from $10^{-4}$ gramion/l fully in accordance with Nernst Law with an EMF-slope of 58 mV/decade. The curves of the four electrodes coincide. The response was tested by a sudden increase in the concentration of the solution in which the electrode was placed from $10^{-4}$ gramion/l to $10^{-3}$ gramion/l and by measuring the EMF relative to a reference electrode as a function of the time. The decrease in the EMF of 58 mV was reached within 5 seconds and remained stable thereafter. If this is compared with a known electrode with a compressed mixture of Ag$_2$S and AgCl then the EMF has decreased by only 45 mV after 90 seconds.

Similar results as with the Ag$_2$S - AgCl electrode according to the invention were obtained with a Ag$_2$S - AgBr and a Ag$_2$S - AgI electrode obtained in this way in Br$^-$ or I$^-$ solutions respectively.

EXAMPLE 2

Ag$_2$S tablets pressed in accordance with example 1 were immersed for 1 hour in a 1 molar solution of CuCl$_2$ in water which had been heated to 50° C. The folowing reaction takes place

$$Ag_2S + Cu^{++} + 2Cl^- \rightarrow 2AgCl + CuS.$$

Thereafter the tablets were leached for 1 minute at 25° C with a 25% ammonia solution and both processes were repeated. The tablets were heated for 2 hours at 200° C in sulphur vapour in a nitrogen atmosphere in order to fix the composition of the copper sulphide.

Figure 2:
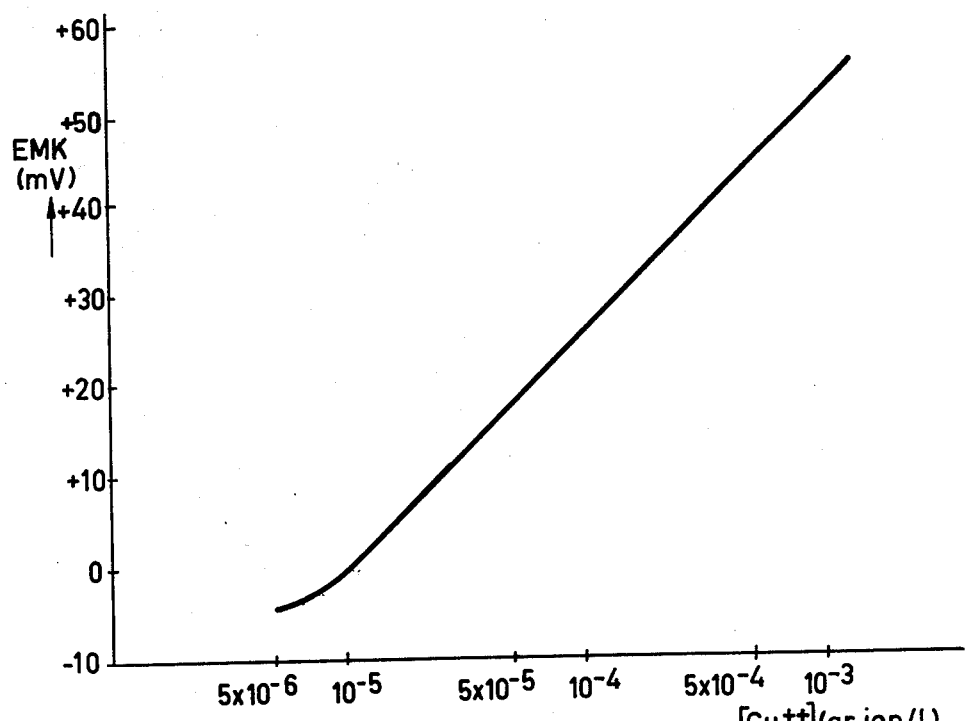

Thereafter EMF measurements were performed with these electrodes in a series of solutions which, besides $10^{-1}$ mole/1NaNO$_3$ also comprised Cu$^{++}$ in a series of concentrations with respect to a saturated calomel electrode. FIG. 2 shows the results of these measurements; mutual deviations between different electrodes relative to one another may be neglected in the scale of the drawing. The variation of the curve from $10^{-5}$ moles/l is again entirely in accordance with Nernst's Law. The speed of response is of the same level as that of the electrode according to example 1.

EXAMPLE 3

An alternative method for making a $Cu^{++}$-electrode as obtained in example 2 consists in that a copper layer, 0,5 μ thick was vacuum-coated on an $Ag_2S$ tablet in vacuo ($5 \times 10^{-6}$ mm). The whole was heated thereafter for 2 hours at 200° C in a tube filled with nitrogen, in which also sulphur was present. The electrode obtained showed fully identical measuring results and a same fast response as that obtained according to example 2.

In a similar manner as described in this and the previous example, ion-selective electrodes for $Pb^{++}$, $Hg^{++}$ and $Cd^{++}$ ions were fabricated, consisting of PbS, HgS, and CdS in the form of a layer on an $Ag_2S$ matrix. The measuring results and response of these electrodes equivalent to those of the CuS electrode.

What is claimed is:

1. A method of producing an ion-selective electrode for selectively measuring the concentration of an ion in a solution of a mixture of ions, said method comprising chemically or electrochemically converting a silver sulfide matrix to the depth of between 0.1 and 100 μm, to an ion sensitive compound having an ion in common with said silver sulfide matrix.

2. A method of producing an ion-selective electrode for selectively measuring the concentration of an ion in a solution of a mixture of ions, said method comprising vacuum depositing a layer having a thickness of between 0.1 to 100 μm on a silver sulfide matrix and chemically converting said layer to an ion-sensitive compound having one ion in common with said silver sulfide matrix.

* * * * *